United States Patent [19]
Hsieh

[11] Patent Number: 5,818,896
[45] Date of Patent: Oct. 6, 1998

[54] METHODS AND APPARATUS FOR THREE-DIMENSIONAL AND MAXIMUM INTENSITY PROJECTION IMAGE RECONSTRUCTION IN A COMPUTED TOMOGRAPHY SYSTEM

[75] Inventor: Jiang Hsieh, Waukesha, Wis.

[73] Assignee: General Electric Company, Milwaukee, Wis.

[21] Appl. No.: 751,648

[22] Filed: Nov. 18, 1996

[51] Int. Cl.⁶ .................................................. A61B 6/03
[52] U.S. Cl. ........................................... 378/15; 378/901
[58] Field of Search ................................... 378/15, 901

[56] References Cited

U.S. PATENT DOCUMENTS

| | | | |
|---|---|---|---|
| 5,454,019 | 9/1995 | Migita et al. ........................... | 378/15 |
| 5,530,731 | 6/1996 | Polacin et al. .......................... | 378/15 |
| 5,625,660 | 4/1997 | Tuy ......................................... | 378/15 |

*Primary Examiner*—David P. Porta
*Assistant Examiner*—David Vernon Bruce
*Attorney, Agent, or Firm*—John S. Beulick; John H. Pilarski

[57] ABSTRACT

The present invention, in one form, is a system for reducing noise artifacts in three-dimensional image reconstruction using data acquired in a helical scan. More specifically, a standard deviation ratio of reconstructed images with and without helical weighting is identified. Such standard deviation ratio is then used to generate filter coefficients, which are then applied to the data in an adaptive smoothing algorithm.

14 Claims, 2 Drawing Sheets

METHODS AND APPARATUS FOR THREE-DIMENSIONAL AND MAXIMUM INTENSITY PROJECTION IMAGE RECONSTRUCTION IN A COMPUTED TOMOGRAPHY SYSTEM

FIELD OF THE INVENTION

This invention relates generally to computed tomography (CT) imaging and more particularly, to three-dimensional and maximum intensity projection image reconstruction in a CT system.

BACKGROUND OF THE INVENTION

In at least one known CT system configuration, an x-ray source projects a fan-shaped beam which is collimated to lie within an X—Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles during one revolution of the x-ray source and detector.

In an axial scan, the projection data is processed to construct an image that corresponds to a two dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a cathode ray tube display.

To reduce the total scan time, a "helical" scan may be performed. To perform a "helical" scan, the patient is moved while the data for the prescribed number of slices is acquired. Such a system generates a single helix from a one fan beam helical scan. The helix mapped out by the fan beam yields projection data from which images in each prescribed slice may be reconstructed.

Reconstruction algorithms for helical scanning typically use helical weighing algorithms which weight the collected data as a function of view angle and detector channel index. Specifically, prior to filtered back projection, the data is weighted according to a helical weighing factor, which is a function of both the gantry angle and detector angle. The helical weighting algorithms also scale the data according to a scaling factor, which is a function of the distance between the x-ray source and the object. The weighted and scaled data is then processed to generate CT numbers and to construct an image that corresponds to a two dimensional slice taken through the object.

It often is desirable to generate three-dimensional (3D) or Maximum Intensity Projection (MIP) images of the object. Known algorithms for generating such images further process the helically weighted and scaled data. For example, to generate an MIP image, a direction of forward projection is determined and a maximum pixel value along each forward projection ray is identified. The projection value is then assigned to this maximum pixel value. To generate a 3D image, boundaries of the object are determined and an imaginary light source is calculated. A shaded surface value of the object is then created based on orientation and the distance of each surface element of the objection with respect to the light source.

The MIP and 3D images typically include noticeable artifacts. Particularly, the helical reconstruction generates image noise which is both non-uniform and non-stationary. This inhomogeneity in noise distribution produces bias, e.g., bright and dark bands or spiral pattern artifacts, in 3D and MIP images.

It would be desirable to provide an algorithm which facilitates the reduction of artifacts in 3D and MIP images due to the inhomogeneous image noise. It also would be desirable to provide such an algorithm which does not significantly increase the processing time.

SUMMARY OF THE INVENTION

These and other objects may be attained in a system which, in one embodiment, includes a smoothing algorithm that generates filter coefficients for reducing noise artifacts. More particularly, and in accordance with one embodiment of the present invention, a standard deviation ratio of reconstructed images with and without helical weighting is identified. This standard deviation ratio, or noise ratio, is then used to generate the filter coefficients, which are applied to either the reconstructed image data or incorporated in the 3D or MIP image generation process.

Specifically, and in accordance with one embodiment, the standard deviation ratio of reconstructed images with and without helical weighting algorithms is identified in accordance with the following:

$$\xi(r, \phi) = \left[ \int_{\beta_o}^{\beta_o + \Pi} w^2(\gamma, \beta) \sigma^2(\gamma, \beta) L'^{-4} d\beta \right]^{1/2} \left[ \int_{\beta_o}^{\beta_o + \Pi} \sigma^2(\gamma, \beta) L'^{-4} d\beta \right]^{-1/2}$$

where:

$\omega(\gamma,\beta)$ is the helical weighting function;

$\sigma(\gamma,\beta)$ is a standard deviation distribution function of the projection;

$\beta$ is a gantry angle;

$\gamma$ is a detector angle; and $L'$ is a projection distance between an x-ray source and a point of interest, $(r,\phi)$.

For a 3×3 kernel size, the filter coefficients are then identified in accordance with:

$$c = \frac{4 - \sqrt{17[0.8\xi'(r,\phi)+1]^{-2} - 1}}{34},$$

where:

$$\xi'(r,\phi) = \begin{cases} \xi(r,\phi) - 0.5 & \text{if } \xi(r,\phi) \geq 0.5 \\ 0 & \text{if } \xi(r,\phi) < 0.5. \end{cases}$$

c is the weight of each surrounding, or neighboring, pixel, 8c is the sum of the surrounding pixel weights, and 1–8c is the weight of the center pixel. The reconstructed image data is then filtered, or adaptively smoothed, in accordance with the determined filter coefficients. Such filtering is described, for example, in N. H. C. Yung and A. H. S. Lai, "Performance evaluation of a feature-preserving filtering algorithm for removing additive random noise in digital images," Optical Engineering, 35(7); 1871–1885 (July 1996).

By generating filter coefficients as described above, and then using such coefficients in an adaptive smoothing process, the reduction of artifacts in 3D or MIP helical image reconstruction may be achieved. Particularly, by adaptively smoothing an image using the above described process, the noise distribution is more uniform thereby reducing, and possibly eliminating, artifacts. Such algorithm also does not significantly increase the processing time.

DETAILED DESCRIPTION OF THE DRAWINGS

Figure 1:
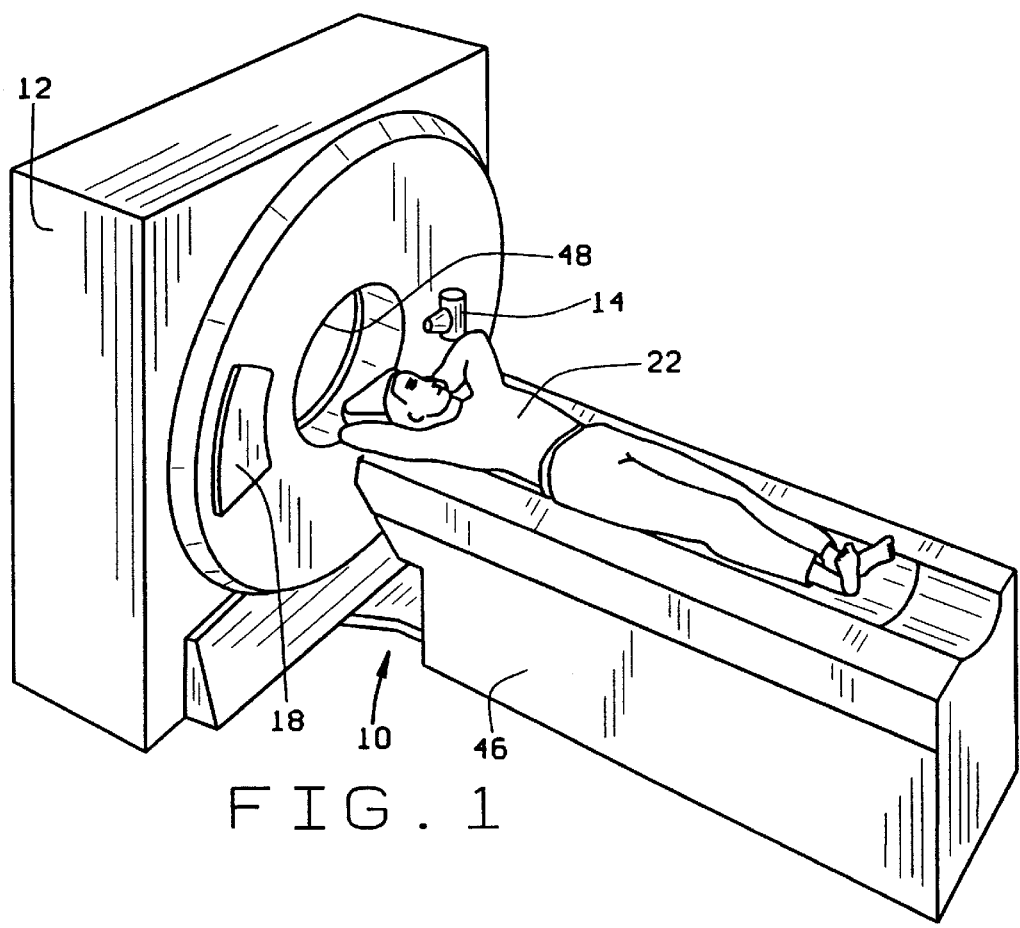
FIG. 1 is a pictorial view of a CT imaging system.
Figure 2:
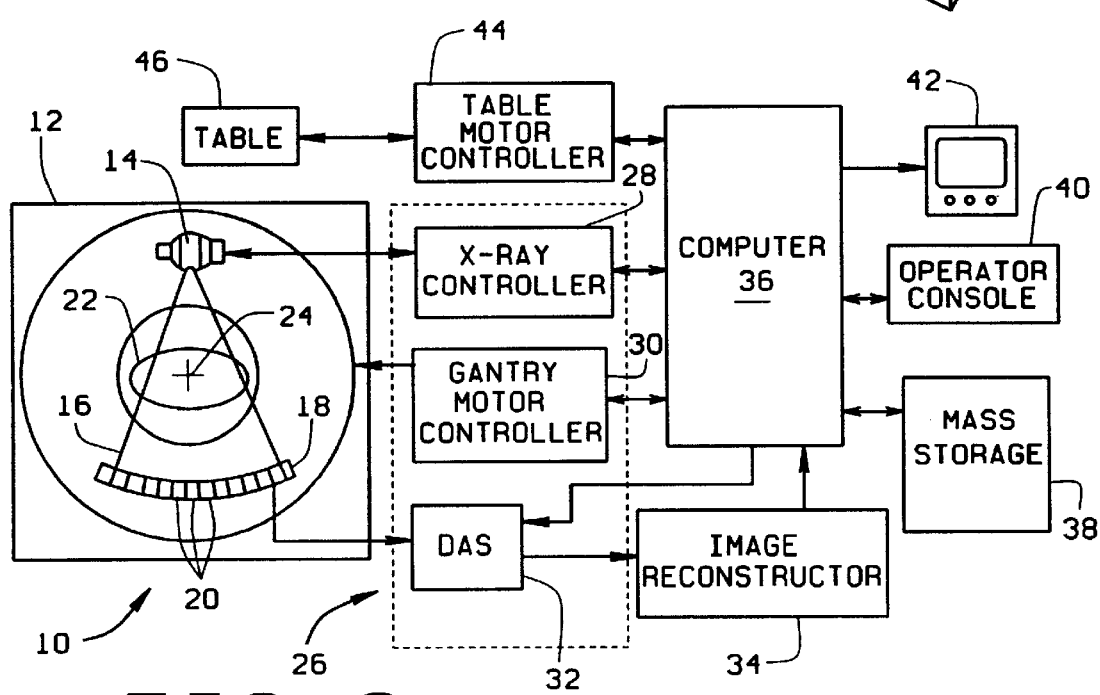
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by detector elements 20 which together sense the projected x-rays that pass through a medical patient 22. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

The known helical reconstruction algorithms may generally be classified as Helical Extrapolative (HE) or Helical Interpolative (HI) algorithms. These algorithms typically apply a weighting factor and a scaling factor to the projection data in order to reconstruct an image. The weighting factor generally is based on both the fan angle and view angle. The scaling factor generally is a function of the distance between patient 22 and x-ray source 14. The reconstructed image data, as described above, typically includes non-stationary noise, i.e., the noise varies in accordance with the scaling factor, the gantry angle, and the view angle.

To generate 3D and Maximum Intensity Projection images, the reconstructed image data typically is further processed. For example, to generate an MIP image, a direction of forward projection is determined and a maximum pixel value along each forward projection ray is identified. The projection value is then assigned to this maximum pixel value. To generate a 3D image, boundaries of the object are determined and an imaginary light source is created. A shaded surface value of the object is then created based on the orientation and the distance of the object with respect to the light source. Such additional processing typically does not reduce the noise artifacts in the reconstructed image data. Accordingly, 3D and Maximum Intensity Projection images often include noticeable artifacts.

Figure 3:
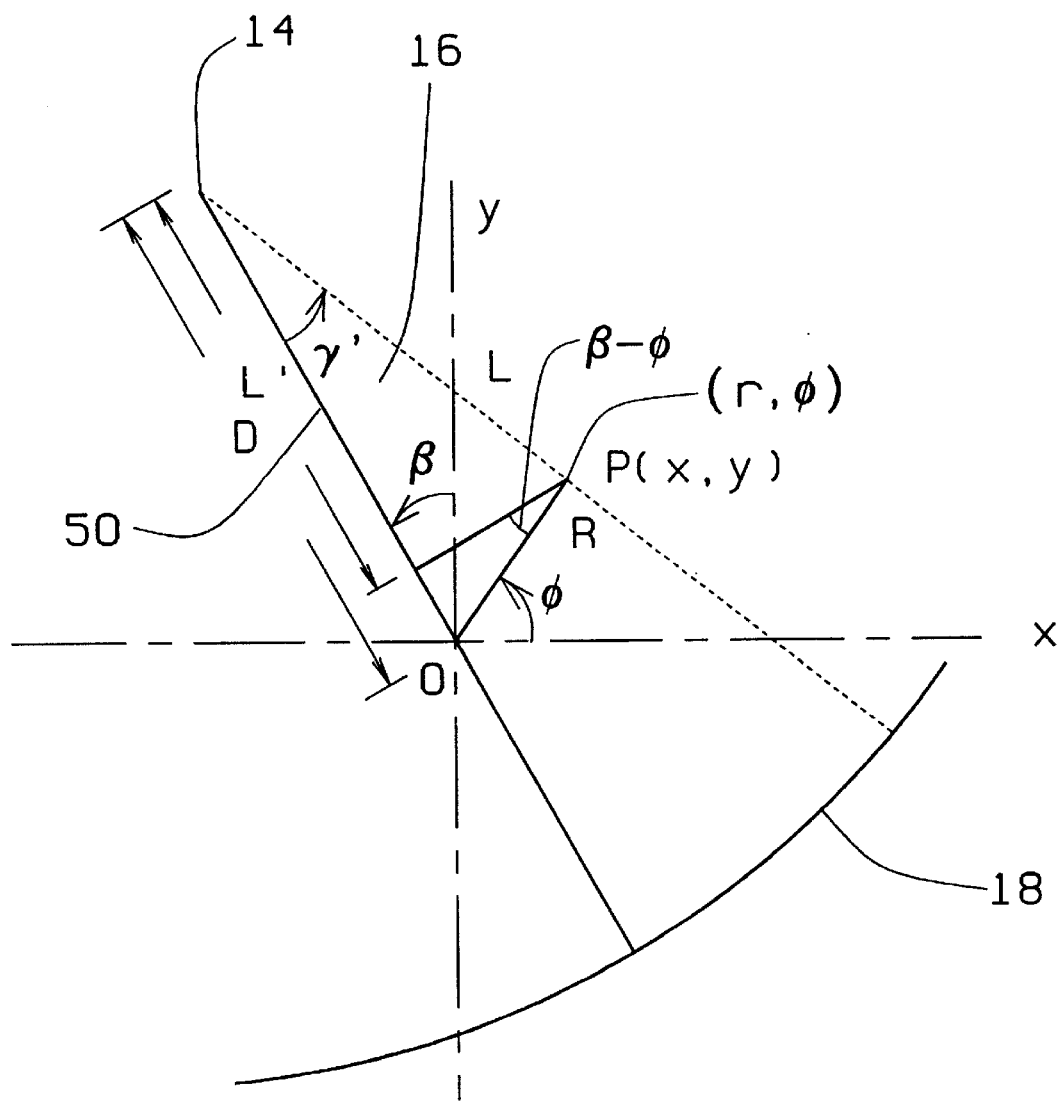
FIG. 3 is a schematic diagram of the geometry of the system illustrated in FIG. 1.

FIG. 3, which is a schematic diagram of the geometry of CT system 10, illustrates detector 18 positioned substantially in the x—y plane P(x,y) of a Cartesian coordinate system having an origin O. X-ray source 14 projects x-ray beam 16, having an iso-center at origin O, toward detector 18 at a gantry angle β and a detector angle γ. For the purpose of the following discussion, D denotes a distance between x-ray source 14 and the iso-center of CT system 10. L denotes a distance between x-ray source 14 and a point of interest (r,φ), where r is a distance between origin O and point of interest (r,φ), and φ is an angle between plane P(x,y) and point of interest (r,φ). A helical reconstruction algorithm ƒ(r,φ) for reconstructing a 3D or MIP image corresponding to point of interest (r,φ) may be defined by the equation:

$$f(r,\phi) = \int_{\beta_o}^{\beta_o + \Pi} \frac{1}{L^2} p(\gamma,\beta) w(\gamma,\beta) g(\gamma' - \gamma) D\cos\gamma d\gamma d\beta \tag{1}$$

where:

p(γ,β) is data, or projections, acquired at detector angle γ and gantry angle β;

φ(γ,β) is the helical weighting function;

D cos γ is the scaling factor;

γ' is a detector angle for point of interest (r,φ) at view angle β; and g(γ) is a convolution reconstruction filter for the fan beam. If ω(γ,β) equals 1 and Π=2π, then equation (1) becomes a conventional fan beam reconstruction formula.

The helical reconstruction algorithm may be simplified by modifying the scaling factor in accordance with the projection of the distance L on a central ray 50 between x-ray source 14 and the iso-center of x-ray beam 16. This projection yields a projection distance L', where L'=L cos γ.

Accordingly, equation (1) can be rewritten as:

$$f(r, \phi) = \int_{\beta_o}^{\beta_o + \Pi} \frac{1}{L'^2} p(\gamma, \beta) w(\gamma, \beta) g(\gamma' - \gamma) D\cos^3\gamma \, d\gamma \, d\beta. \quad (2)$$

Helical reconstruction algorithm $f(r,\phi)$, as previously described, converts the projections $\rho(\gamma,\beta)$ into integers, also called CT numbers, which are used to control the brightness of corresponding pixels on display 42. This conversion, or data processing, however, is known to generate noise artifacts, and thus generates bright and dark bands or spirals in 3D and MIP images.

The noise generated by helical reconstruction algorithm $f(r,\phi)$ is directly related to the helical weighting function $\omega(\gamma,\beta)$ and the scaling factor $L'^{-2}$ in the backprojection process. Particularly, and where $\sigma(\gamma,\beta)$ is a standard deviation distribution function of the projection, a standard deviation ratio of data processed with the weighting schemes and without the weighting schemes may be described in accordance with the equation:

$$\xi(r, \phi) = \left[ \int_{\beta_o}^{\beta_o + \Pi} w^2(\gamma, \beta)\sigma^2(\gamma, \beta) L'^{-4} d\beta \right]^{1/2} \left[ \int_{\beta_o}^{\beta_o + \Pi} \sigma^2(\gamma, \beta) L'^{-4} d\beta \right]^{-1/2} \quad (3)$$

This ratio is also referred to hereinafter as the noise ratio.

As shown in equation (3), the location of point of interest $(r,\phi)$ directly affects image noise. Particularly, noise ratio $\xi(r,\phi)$ differs significantly between a first location $(r_1,\phi_1)$ and a second location $(r_2,\phi_2)$. At some locations, noise ratio $\xi(r,\phi)$ approximates 0.5, while noise ratio $\xi(r,\phi)$ approximates 2.0 at other locations. Accordingly, the generated noise is both non-uniform and non-stationary, i.e., the noise pattern varies with respect to detector angle $\gamma$, gantry angle $\beta$, and distance L. This inhomogeneity in noise distribution results in bias, e.g., bright and dark band or spiral pattern artifacts, in generated 3D and MIP images.

In accordance with one embodiment of the present invention, a smoothing algorithm reduces noise artifacts by providing a substantially uniform noise distribution in the displayed image. The present smoothing algorithm is not directed to, nor limited to practice with, any particular helical image reconstruction algorithm. Rather, the present smoothing algorithm may be used in conjunction with many different helical reconstruction algorithms. Also, although the present smoothing algorithm is sometimes described herein in connection with a third generation CT system, the present algorithm can be practiced in connection with many other types of CT systems, including fourth generation CT systems. Further, in one embodiment, the smoothing algorithm would be implemented in computer 36 and would process, for example, data stored in mass storage 38. Many other alternative implementations are, of course, possible.

In accordance with one embodiment of the present invention, the adaptive smoothing is performed using filter coefficients which smooth, or provide a more uniform distribution, of image noise in a 3D or MIP image. Particularly, in the one embodiment, the helical weighting function $\omega(\gamma,\beta)$ is generated, and the filter coefficients are generated in accordance with, i.e., based on, the standard deviation ratio $\xi(r,\phi)$. The filter coefficients are then utilized in the filtering, or smoothing, so that a substantially uniform noise distribution results in the image.

As one specific example, when a 3×3 kernel is utilized to perform the smoothing, filter coefficients are determined in accordance with the equation:

$$c = \frac{4 - \sqrt{17[0.8\xi'(r, \phi) + 1]^{-2} - 1}}{34}, \quad (4)$$

where:

$$\xi'(r, \phi) = \begin{cases} \xi(r, \phi) - 0.5 & \text{if } \xi(r, \phi) \geq 0.5 \\ 0 & \text{if } \xi(r, \phi) < 0.5. \end{cases} \quad (5)$$

c is the weight in the neighboring pixels, and 1–8c is the weight of the center pixel. These identified weights, or coefficients, are then utilized in the kernel and applied to the data to adaptively smooth the image. The "smoothing" is performed directly on the data before the 3D or MIP reconstruction process, or the algorithm may be performed during the 3D or MIP image reconstruction process.

To substantially maintain image resolution, i.e., to reduce any impact of the smoothing algorithm on image resolution, the data may be segmented into "smoothed data" and "non-smoothed data" prior to execution of the smoothing algorithm. Such segmenting may be performed, for example, by grey scale thresholding. The "non-smoothed data", i.e., the data whose value difference from the center pixel exceeds a selected threshold value, are excluded from the determination of filter coefficients c. The filter coefficients c are determined on the basis of only the "smoothed data".

The above described algorithm facilitates reducing artifacts in 3D and MIP helical image reconstruction. Such algorithm also is not believed to significantly increase the processing time needed to generate such images.

From the preceding description of various embodiments of the present invention, it is evident that the objects of the invention are attained. Although the invention has been described and illustrated in detail, it is to be clearly understood that the same is intended by way of illustration and example only and is not to be taken by way of limitation. For example, the CT system described herein is a "third generation" system in which both the x-ray source and detector rotate with the gantry. Many other CT systems including "fourth generation" systems wherein the detector is a full-ring stationary detector and only the x-ray source rotates with the gantry, may be used. Accordingly, the spirit and scope of the invention are to be limited only by the terms of the appended claims.

What is claimed is:

1. A system for generating an image of an object using data acquired in a helical scan, said system comprising an x-ray source and a detector array, said system configured to:
   determine a helical weighting function;
   determine a standard deviation ratio of reconstructed images with and without helical weighting;
   identify a filter coefficient based at least in part on the determined standard deviation ratio; and
   apply the identified filter coefficient to the data.

2. A system in accordance with claim 1 wherein to identify the filter coefficient, said system is further configured to segment the data.

3. A system in accordance with claim 2 wherein to segment the data, said system is configured to perform grey scale thresholding.

4. A system in accordance with claim 1 further configured to generate a Maximum Intensity Projection image.

5. A system in accordance with claim 1 wherein said standard deviation ratio of reconstructed images with and without helical weighting is:

$$\xi(r, \phi) = \left[ \int_{\beta_o}^{\beta_o + \Pi} w^2(\gamma, \beta)\sigma^2(\gamma, \beta)L'^{-4}d\beta \right]^{1/2} \left[ \int_{\beta_o}^{\beta_o + \Pi} \sigma^2(\gamma, \beta)L'^{-4}d\beta \right]^{-1/2}$$

where:
  $\omega(\gamma,\beta)$ is the helical weighting function;
  $\sigma(\gamma,\beta)$ is a standard deviation distribution function of the projection;
  $\beta$ is a gantry angle;
  $\gamma$ is a detector angle;
  L' is a projection distance between an x-ray source and a point of interest, $(r,\phi)$.

6. A system in accordance with claim 5 further comprising a 3×3 kernel, and wherein the filter coefficient is identified according to:

$$c = \frac{4 - \sqrt{17[0.8\xi'(r, \phi) + 1]^{-2} - 1}}{34}$$

-continued where:

$$\xi'(r, \phi) = \begin{cases} \xi(r, \phi) - 0.5 & \text{if } \xi(r, \phi) \geq 0.5 \\ 0 & \text{if } \xi(r, \phi) < 0.5. \end{cases}$$

7. A system in accordance with claim 1 further configured to generate a three-dimensional image.

8. A method for generating an image of an object using data acquired in a helical scan, said method comprising the steps of:
  determining a helical weighting function;
  determining a standard deviation ratio of reconstructed images with and without helical weighting;
  identifying a filter coefficient based at least in part on the determined standard deviation ratio; and
  applying the identified filter coefficient to the data.

9. A method in accordance with claim 8 further comprising the step of generating a Maximum Intensity Projection image.

10. A method in accordance with claim 8 wherein identifying the filter coefficient comprises the step of segmenting the data.

11. A method in accordance with claim 10 wherein segmenting the data comprises the step of performing grey scale thresholding.

12. A method in accordance with claim 8 further comprising the step of generating a three-dimensional image.

13. A method in accordance with claim 8 wherein the standard deviation ratio of reconstructed images with and without helical weighting is:

$$\xi(r, \phi) = \left[ \int_{\beta_o}^{\beta_o + \Pi} w^2(\gamma, \beta)\sigma^2(\gamma, \beta)L'^{-4}d\beta \right]^{1/2} \left[ \int_{\beta_o}^{\beta_o + \Pi} \sigma^2(\gamma, \beta)L'^{-4}d\beta \right]^{-1/2}$$

where:
  $\omega(\gamma,\beta)$ is the helical weighting function;
  $\sigma(\gamma,\beta)$ is a standard deviation distribution function of the projection;
  $\beta$ is a gantry angle;
  $\gamma$ is a detector angle;
  L' is a projection distance between an x-ray source and a point of interest, $(r,\phi)$.

14. A method in accordance with claim 13 wherein the filter coefficient is identified according to:

$$c = \frac{4 - \sqrt{17[0.8\xi'(r, \phi) + 1]^{-2} - 1}}{34}$$

where:

$$\xi'(r, \phi) = \begin{cases} \xi(r, \phi) - 0.5 & \text{if } \xi(r, \phi) \geq 0.5 \\ 0 & \text{if } \xi(r, \phi) < 0.5. \end{cases}$$

* * * * *